United States Patent [19]

Horner et al.

[11] 4,344,886
[45] Aug. 17, 1982

[54] PREPARATION OF 2-HYDROXYALKYLCHROMANS

[75] Inventors: Michael Horner, Neustadt; Axel Nissen, Leimen, both of Fed. Rep. of Germany

[73] Assignee: BASF Aktiengesellschaft, Fed. Rep. of Germany

[21] Appl. No.: 238,608

[22] Filed: Feb. 26, 1981

[30] Foreign Application Priority Data

Mar. 19, 1980 [DE] Fed. Rep. of Germany ....... 3010504

[51] Int. Cl.³ .......................................... C07D 311/72
[52] U.S. Cl. ....................................................... 549/408
[58] Field of Search ..................................... 260/345.5

[56] References Cited

U.S. PATENT DOCUMENTS

| | | | |
|---|---|---|---|
| 2,411,969 | 12/1946 | Karrer et al. | 260/345.5 |
| 3,444,213 | 5/1969 | Nelan | 260/345.5 |
| 4,026,907 | 5/1977 | Scott et al. | 260/345.5 |
| 4,191,692 | 3/1980 | Grafen et al. | 260/345.5 |

FOREIGN PATENT DOCUMENTS 2364141 6/1974 Fed. Rep. of Germany ... 260/345.5

Primary Examiner—Nicky Chan
Attorney, Agent, or Firm—Keil & Witherspoon

[57] ABSTRACT

2-Hydroxyalkylchromans (I)

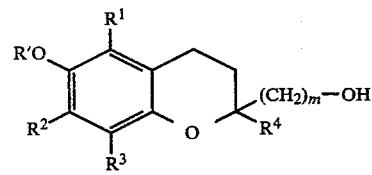

where $R^1$, $R^2$, $R^3$ and $R^4$ are each H or $C_1$–$C_8$-alkyl, $R'$ is H or an organic radical which can be split off hydrolytically or hydrogenolytically as $R'$-OH or $R'$-COOH, and m is 1, 2 or 3, are prepared by reacting a hydroquinone II

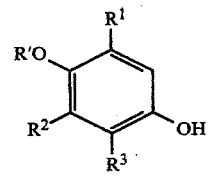

(a) with an alkenediol IIIa

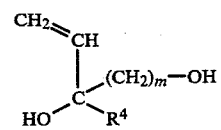

or
(b) with an alkenediol IIIb

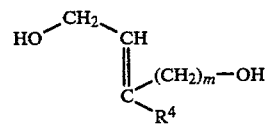

or
(c) with an alkenediol IIIc

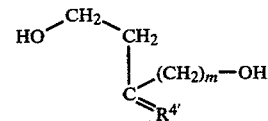

where $R^{4'}$ is a radical which during the condensation with II is converted to the radical $R^4$, at from $-50°$ C. to $120°$ C., in an inert solvent, in the presence of from 10 to 300 mole %, based on II, of a Lewis acid or of an adduct of a Lewis acid with a Lewis base which has a lower basicity than compound II.

2 Claims, No Drawings

PREPARATION OF 2-HYDROXYALKYLCHROMANS

The present invention relates to a novel process for the preparation of 2-hydroxyalkylchromans of the general formula I

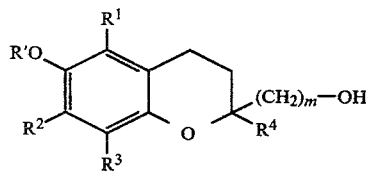

where $R^1$, $R^2$, $R^3$ and $R^4$ are each H or $C_1$–$C_8$-alkyl, R' is H or an organic radical which can be split off hydrolytically or hydrogenolytically as R'-OH or R'-COOH, and m is 1, 2 or 3.

Compounds of this type are disclosed in German Laid-Open Application DOS 2,364,141. According to the process described there, they are prepared by reacting a hydroquinone (II)

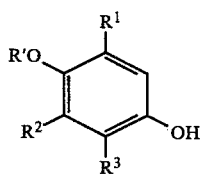

with an alkenediol monoether or alkenediol monoester (III')

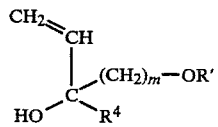

in the presence of an acidic catalyst. The acidic catalysts recommended are Lewis acids, inorganic acids or mixtures of Lewis acids and inorganic acids, and in particular a mixture of hydrochloric acid and zinc chloride.

However, this process is involved and uneconomical, since it necessitates first preparing monoethers or monoesters of the diols IIIa

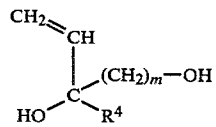

on which the compounds III' are based.

It is an object of the present invention to provide a method of preparing the 2-hydroxyalkylchromans I directly from the hydroquinones II and the free alkenediols IIIa or other alkenediols suitable as synthesis starting materials.

We have found that this object is achieved and that 2-hydroxyalkylchromans of the general formula I

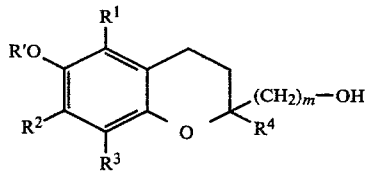

where $R^1$, $R^2$, $R^3$ and $R^4$ are each H or $C_1$–$C_8$–alkyl, R' is H or an organic radical which can be split off hydrolytically or hydrogenolytically as R'-OH or R'-COOH, and m is 1, 2 or 3 are obtained in a simple and economical manner by reacting a hydroquinone II

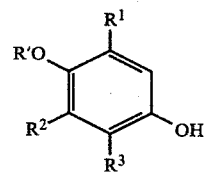

(a) with an alkenediol IIIa

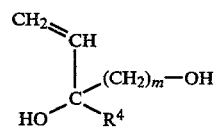

or
(b) with an alkenediol IIIb

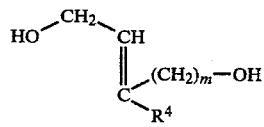

or
(c) with an alkenediol IIIc

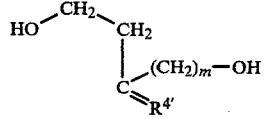

where $R^{4'}$ is a radical which during the condensation with II is converted to the radical $R^4$,
at from $-50°$ C. to 120° C., in an inert solvent, in the presence of from 10 to 300 mole %, based on II, of a Lewis acid or of an adduct of a Lewis acid with a Lewis base which has a lower basicity than compound II.

The hydroquinones II used as starting compounds are known or, if not, are obtainable by conventional methods. From the point of view of the properties of the products and of the ease of preparation of the hydroquinone II, trimethylhydroquinone is the most important.

If $R^1$ and/or $R^2$ is hydrogen, it is advisable to protect the OH group, located between them, by etherification or esterification, by means of an alcohol R'-OH or an acid R'-COOH respectively, in a conventional manner, to ensure that different cycloaddition products of II with the alkenediol III are not obtained. In principle, the radical R' in the protective group may be any organic radical which for its part must of course not carry any substituent which might cause interfering side-reactions. However, for practical reasons, protective groups in which R' is $C_1$-$C_4$-alkyl or benzyl are used. After completion of the synthesis, the protective group is again removed in a conventional manner by hydrolysis or hydrogenation. Even where $R^1$ and/or $R^2$ are not H, it may be advisable to carry out the reaction with the OH group appropriately protected, especially if the hydroquinone II is in any case obtained in a protected form from its method of synthesis.

The starting compounds III (IIIa, IIIb and IIIc) are known or may be obtained by conventional methods. In general, those compounds III where $R^4$ is hydrogen or especially methyl are preferred.

Accordingly, suitable alkenediols IIIa are especially but-3-ene-1,2-diol, pent-4-ene-1,3-diol, 2-methylbut-3-ene-1,2-diol and 3-methylpent-4-ene-1,3-diol. These compounds are obtained by partially hydrogenating the corresponding alkynediols, by reacting carbonyl compounds $R^4$—CO—$(CH_2)_m$—OH with vinyl-MgCl or by rearrangement of the compounds IIIb.

Particularly suitable alkenediols IIIb are but-2-ene-1,4-diol, pent-2-ene-1,5-diol, 2-methylbut-2-ene-1,4-diol and 3-methylpent-2-ene-1,5-diol.

These compounds may be obtained by partially hydrogenating the corresponding alkynediols or by oxidative adduct formation of acetic acid with 1,3-dienes, followed by hydrolysis, and also by isomerization of the compounds IIIc.

The preferred alkenediols IIIc, namely 2-methylenebutane-1,4-diol and 3-methylenepentane-1,5-diol, may be obtained by isomerization of the compounds IIIb.

Examples of suitable Lewis acids are boron halides, eg. $BF_3$ and $BCl_3$, aluminum halides, eg. $AlCl_3$ and $AlBr_3$, tin tetrahalides, eg. $SnCl_4$ and $SnBr_4$, and antimony trihalides, eg. $SbF_3$ and $SbCl_3$.

Adducts of Lewis acids with Lewis bases of lower base strength than that of compound II may also be used. Such compounds are, inter alia, adducts of the above Lewis acids with ethers, eg. dimethyl ether, diethyl ether and tetrahydrofuran, esters, eg. ethyl acetate, and organic nitro compounds, eg. nitromethane, nitropropane, nitrobenzene and the nitrotoluenes. Amongst the Lewis acids and Lewis acid/Lewis base adducts, $BF_3$, $AlCl_2$ and $BF_3$-diethyl etherate are preferred.

The amount of Lewis acid or adduct used is in general from 10 to 300 mole %, based on the hydroquinone, but amounts of from 50 to 200, and especially from 80 to 120, mole % are as a rule preferred.

Suitable inert solvents are in general aprotic liquids having a donicity of at most 20. The concept of donicity is defined in the work of V. Gutmann, Angew. Chemie, 82 (1972), 858. It expresses the affinity to Lewis acids and means, in the case of the present proviso, that the solvent should not form a stable adduct complex with Lewis acids. Accordingly, examples of suitable solvents are methylene chloride, 1,2-dichloroethane, chloroform, benzene, toluene, chlorobenzene, nitromethane, nitrobenzene, benzonitrile, acetonitrile, cyclohexane and mixtures of these solvents.

Amongst the stated solvents, mixtures of toluene or methylene chloride with nitromethane are particularly suitable. The function of the solvent is to keep at least a proportion of the reactants employed in homogeneous solution. The amount of solvent can vary within wide limits but is in general from 1 to 10 kg per kg of II.

The reaction temperatures are preferably from −50° to 100° C., especially from −40° to 60° C. Since the reaction can under certain circumstances take place very vigorously, which can lead to increased formation of undesired products, it is advisable to start the reaction at a low temperature and then to raise the temperature gradually. Excessively vigorous reaction can also be avoided by adding the reactants gradually.

Since the reaction can be carried out under atmospheric pressure there is as a rule no reason to carry it out under reduced pressure or superatmospheric pressure.

There are no other technical aspects of the process which require special attention, ie. the reaction can be carried out by the conventional preparative techniques, for example by taking a solution or suspension of the hydroquinone II and gradually and simultaneously adding a solution of an alkenediol III and the Lewis acid or a solution of the Lewis acid or of the Lewis acid adduct.

The reaction mixtures can be worked up by conventional methods known for Friedel-Crafts reactions, for example by adding water, with or without ether, to the mixture and distilling the solvent from the dried organic phase. The crude product thus obtained, which contains compound I in from about 50 to 90% yield, can, if desired, be purified by recrystallization, for example from acetone/water. In most cases, however, the products crystallize out in a very pure form from the organic phase obtained after hydrolysis, so that further purification is unnecessary.

The 2-hydroxyalkylchromans I are important intermediates for the preparation of vitamin E and of related antioxidants, which in turn are used as stabilizers for organic materials such as fats, oils and plastics.

EXAMPLES 1 to 14

Preparation of 2,5,7,8-tetramethyl-6-hydroxy-2-(2-hydroxyethyl)-chroman (Ia)

EXAMPLE 1

Preparation of Ia from 3-methylpent-2-ene-1,5-diol 128 g (0.845 mole) of trimethylhydroquinone, followed by 98 g (0.845 mole) of 3-methylpent-2-ene-1,5-diol, were added to a solution of 112.5 g (0.84 mole) of $AlCl_3$, 750 ml of methylene chloride and 100 ml of nitromethane at −10° C. The solution was then stirred for 10 hours at room temperature.

To work up the mixture, the brown reaction solution obtained was hydrolyzed with 150 ml of water, whilst cooling; the product precipitated in a crystalline form. This precipitate was washed twice with water, and dried. The yield of Ia was 83%. A further 8% were obtained from the liquid phase of the hydrolysis mixture, by concentrating this phase and extracting the residue with toluene. Melting point of Ia: 118°–120° C.

EXAMPLE 2

Preparation of Ia from 3-methylpent-4-ene-1,3-diol 25 g (0.16 mole) of trimethylhydroquinone were added to a solution of 21.9 g (0.164 mole) of $AlCl_3$, 150 ml of methylene chloride and 20 ml of nitromethane at −10° C., 19.1 g (0.164 mole) of 3-methylpent-4-ene-1,3-diol were then introduced in the course of 25 minutes, and thereafter the mixture was stirred for 12 hours at room temperature. Working up the reaction mixture by a method similar to Example 1 gave the chroman derivative Ia in 78% yield.

EXAMPLE 3

Preparation of Ia from 3-methylenepentane-1,5-diol

The above diol was converted to the chroman derivative Ia, in 51% yield based on hydroquinone employed, by proceeding as described in Example 2, but using ethylene chloride instead of methylene chloride.

EXAMPLES 4 TO 14

Preparation of Ia from 3-methylpent-2-ene-1,5-diol, using various Lewis acids.

Ia was prepared by the method described in Example 1, but with the same molar amounts of other Lewis acids than AlCl₃; the results are shown in the Table below.

| Example No. | Lewis acid | Conversion, based on TMH[x] % | Yield, based on TMH[x] employed % |
|---|---|---|---|
| 1 | AlCl₃ | 99 | 91 |
| 4 | BF₃ | 91 | 79 |
| 5 | BF₃.OEt₂ | 70 | 63 |
| 6 | AlBr₃ | 95 | 85 |
| 7 | ZnCl₂ | 78 | 39 |
| 8 | ZnBr₂ | 84 | 68 |
| 9 | ZnI₂ | 95 | 23 |
| 10 | SnCl₄ | 93 | 60 |
| 11 | SnBr₄ | 96 | 66 |
| 12 | BCl₃ | 58 | 39 |
| 13 | SbCl₃ | 95 | 69 |
| 14 | SbF₃ | 55 | 27 |

[x]trimethylhydroquinone

EXAMPLE 15

Preparation of 2,5,7,8-tetramethyl-6-hydroxy-2-hydroxymethyl-chroman (Ib)

This compound was prepared by a method similar to Example 1, but using 2-methylbut-2-ene-1,4-diol instead of the pentenediol. The yield of Ib was 10%; melting point 123°–125° C. (after recrystallization from diethyl ether/petroleum ether).

We claim:

1. A process for the preparation of a 2-hydroxyalkyl-chroman of the formula I

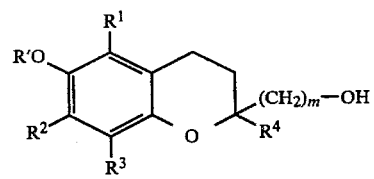

where $R^1$, $R^2$, $R^3$ and $R^4$ are each H or $C_1$–$C_8$-alkyl, $R'$ is H or an organic radical which can be split off hydrolytically or hydrogenolytically as $R'$-OH or $R'$-COOH, and m is 1, 2 or 3, wherein a hydroquinone II

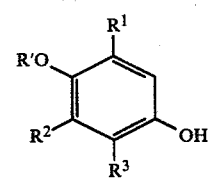

is reacted
(a) with an alkenediol IIIa

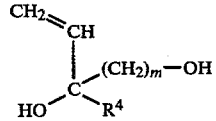

or
(b) with an alkenediol IIIb

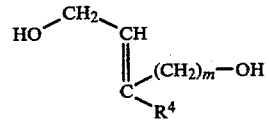

or
(c) with an alkenediol IIIc

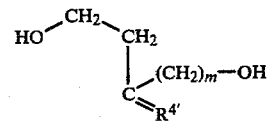

where $R^{4'}$ is methylene, at from −50° C. to 120° C., in an inert solvent, in the presence of from 10 to 300 mole %, based on II, of a Lewis acid or of an adduct of a Lewis acid with a Lewis base which has a lower basicity than compound II.

2. A process as defined in claim 1, wherein $R^4$ is H or $CH_3$.

* * * * *